United States Patent [19]

Buffet

[11] Patent Number: 4,846,180

[45] Date of Patent: Jul. 11, 1989

[54] ADJUSTABLE IMPLANTABLE HEART STIMULATOR AND METHOD OF USE

[75] Inventor: Jacques Buffet, Villemomble, France

[73] Assignee: Compagnie Financiere St.-Nicolas, Le Raincy, France

[21] Appl. No.: 107,480

[22] Filed: Oct. 13, 1987

[30] Foreign Application Priority Data

Oct. 13, 1986 [FR] France ............................... 86 14187

[51] Int. Cl.$^4$ .............................................. A61N 1/36
[52] U.S. Cl. ................................................ 128/419 P
[58] Field of Search ...... 128/419 P, 419 PG, 419 PT, 128/419 R

[56] References Cited

U.S. PATENT DOCUMENTS

| | | | |
|---|---|---|---|
| 3,867,950 | 2/1975 | Fischell | 128/419 P |
| 4,592,360 | 6/1986 | Lesnick | 128/419 PG |
| 4,699,143 | 10/1987 | Dufresne et al. | 128/419 R |
| 4,712,179 | 12/1987 | Heimer | 128/419 PT |

FOREIGN PATENT DOCUMENTS

| | | |
|---|---|---|
| 96464 | 12/1983 | European Pat. Off. |
| 2342722 | 3/1977 | France |
| 2374024 | 12/1977 | France |
| 2379104 | 1/1978 | France |
| 2383674 | 3/1978 | France |
| 2424737 | 5/1978 | France |
| 2427737 | 5/1978 | France |
| 2431296 | 6/1979 | France |
| 2471789 | 12/1979 | France |
| 2481933 | 11/1980 | France |
| 2516797 | 11/1982 | France |
| 2550095 | 8/1983 | France |

Primary Examiner—Francis Jaworski
Attorney, Agent, or Firm—Mason, Fenwick & Lawrence

[57] ABSTRACT

A method and apparatus for adjusting an implantable heart stimulator (1) in dependence on the effort exerted by the patient wearing the stimulator, using an external control programmer (2) associated in operation with the stimulator (1), a number of typical operating programs $p_i$ of the stimulator (1) being previously defined, each corresponding to a type of effort by the patient and characterized by specific values v of at least one operating parameter p of the stimulator (1), and the stimulator (1) is externally actuated, via the control programmer (2), so as to select the desired operating program $p_i$, the result of the selection being that the stimulator (1) then operates in accordance with the selected operating program, so that the patient can automatically choose an operating program $p_i$ for the stimulator (1) in dependence on an effort to be made. The typical operating programs $p_i$ and consequently the specific values V of the parameters p, i.e., the maximum stimulation frequency F and the time D necessary for reaching the frequency F, are stored in the memory of a microprocessor (3) found in the stimulator (1).

5 Claims, 1 Drawing Sheet

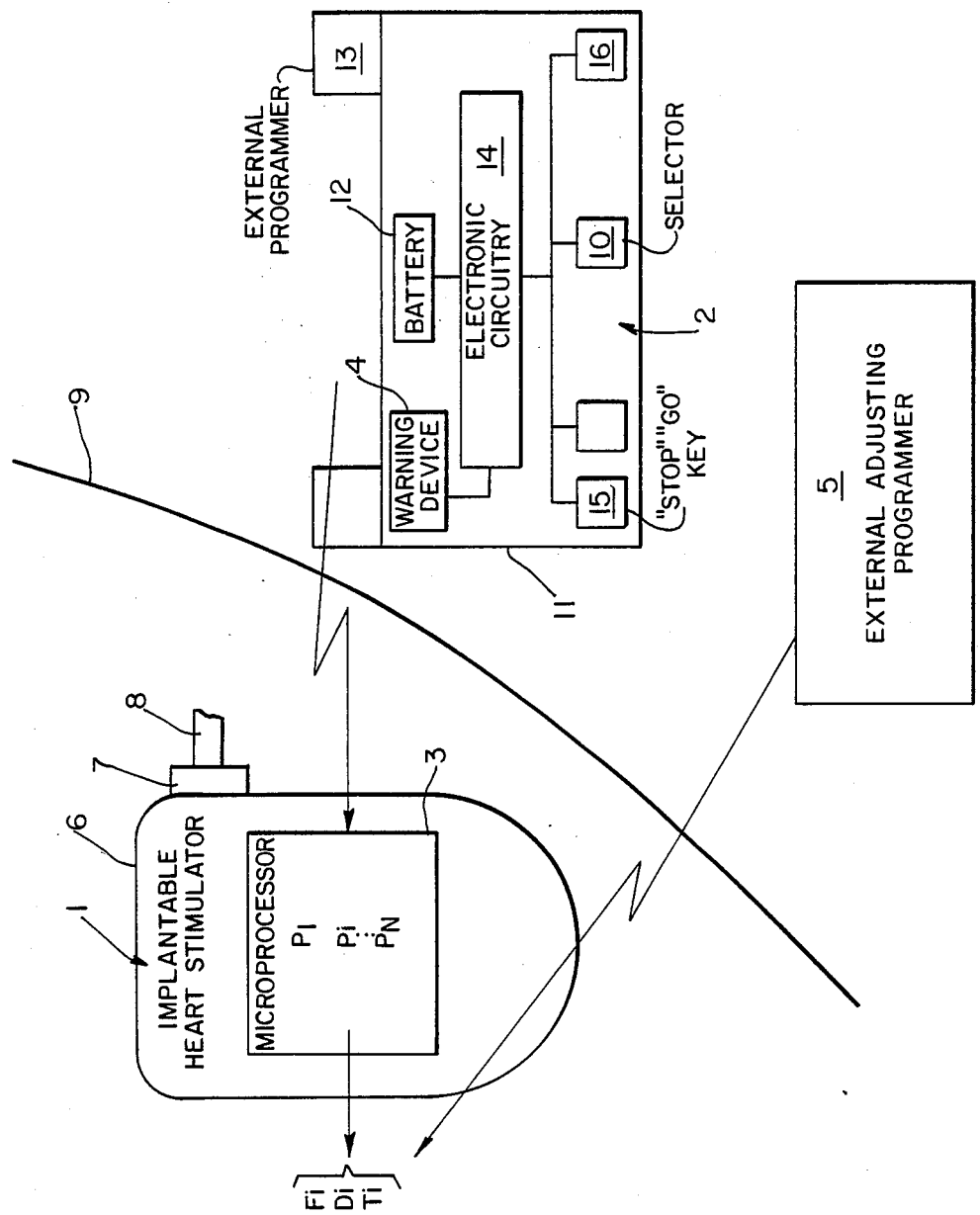

ADJUSTABLE IMPLANTABLE HEART STIMULATOR AND METHOD OF USE

BACKGROUND OF THE INVENTION

The invention relates to a method of adjusting an implantable heart stimulator in dependence on the effort exerted by the patient wearing the stimulator, using an external control programmer associated in operation with the stimulator, an implantable heart stimulator having parameters adjustable in dependence on the effort exerted by the patient, and an external programmer for actuating an implantable heart stimulator so as to adjust the operating parameters of the stimulator, which comprises receiving means for coupling to the programmer.

Known adjustable heart stimulators (French PSS 2 379 104, 2 383 674, 2, 471 789, 2 431 296, 2 424 737, 2 342 722, 2 374 024, 2 550 095, 2 516 797, European PS 96 464, U.S. Pat. No. 3,867,950) are of one of the following two kinds, externally controlled or internally controlled, the two kinds not being exclusive of one another.

Known external control is brought about via an external programmer, usually by the doctor, and the aim is to adapt when necessary (usually occasionally) the various parameters of the stimulator (the stimulation period, width of stimulation pulse, amplitude of stimulation pulse, sensitivity of amplifier of stimulator, refractory period, escape period, etc.). In the first case, the programmer and the stimulator are designed so that the parameters can be adjusted separately and in succession. This adjustment takes time and requires supervision by the doctor, which is not troublesome in itself, since the adjustment is occasional. A typical embodiment of an aforementioned stimulator is described in French PS 2 427 737. Another typical example is a stimulator having two switchable speeds; a powerful magnetic disposed opposite the place where the stimulator is implanted produces a magnetic field so as to flip the stimulator from a first operating speed to a second operating speed and thus adapt it to requirements. This embodiment has the advantage of simplicity but the disadvantage of being of limited range.

Known internal control is usually brought about automatically, depending on the state of the patient wearing the stimulator, via a parameter representing his state. There are various typical known embodiments: a stimulator actuated by auricular activity or the temperature of the venous flow or frequency of respiration or the distance between the R wave and the apex of the T wave of cardiac activity etc. These embodiments have the advantage of automatic adjustment but present numerous problems—unreliable maintenance of position of an auricular electrode for recording the auricular electric activity, defective correlation between the measured parameter and the values given to the operating parameter of the stimulator, and difficulties in accurately determining the position of the T wave etc. in dependence on the parameter under consideration.

There is also a known heart stimulator programmer (document FR 2481933) which can be operated by the patient himself, the programmer comprising a slider for selecting one out of three operating frequencies of the heart stimulator, or more specifically the frequency corresponding to a particular physiological need. However, this programmer has some disadvantages; the change from one to another frequency occurs abruptly, the patient risks forgetting the frequency at which his stimulator is operating, programmers are specific and non-interchangeable, the operating modes of the stimulator are undeveloped, the programmer can be forcibly misadjusted and altered, and the programmer in use has to be disposed opposite the stimulator, which is inconvenient. In short there is some risk in operation, and the equipment is expensive and unsophisticated.

SUMMARY OF THE INVENTION

The invention aims to provide a stimulator which is externally adjustable in dependence on the efforts exerted by the patient and which is simple in construction and operation but permits relatively wide adjustment of the parameters.

Another aim is to provide an aforementioned stimulator which is automatically adjustable, i.e. adjustable by the patient himself.

To this end, the invention firstly proposes a method of adjusting an implantable heart stimulator in dependence on the effort exerted by the patient wearing the stimulator, using an external control programmer associated in operation with the stimulator, a number of typical operating programmes of the stimulator being previously defined, each corresponding to a type of effort by the patient and characterised by specific values of at least one operating parameter of the stimulator, and the stimulator is externally actuated, via the control programmer, so as to select the desired typical operating program, the result of the selection being that the stimulator then operates in accordance with the selected typical program, so that the patient can automatically choose a typical operating program for the stimulator in dependence on an effort to be made, characterised in that the typical programs and consequently the specific value of the parameters, i.e. the maximum stimulation frequency and the time D necessary for reaching the frequency, are stored in the memory of a microprocessor for the stimulator.

Secondly, the invention proposes an implantable heart stimulator having parameters adjustable in dependence on the effort exerted by the patient, using means for externally selecting a typical operating program, characterised in that the stimulator comprises a microprocessor having a memory for storing a number of typical operating programs characterised by specific values of at least one operating parameter of the stimulator.

Finally the invention proposes an external programmer for actuating an implantable cardiac stimulator for adjusting the operating parameters of the stimulator, the stimulator comprising receiving means adapted to be coupled to the programmer which is characterised in that it comprises at least one selector of a typical program out of a number of types characterised by specific values of at least one parameter of the stimulator, i.e. a casing, a source of electric energy such as a battery disposed in the casing, electric contacts for transmitting electric pulses to the heart stimulator so as to actuate it, and an electronic circuit associated with the electric energy source, the contacts and the selector being adapted to supply the contacts with specific pulse trains depending on the state of the selector.

According to another optional feature of the invention, the specific values of the parameters of each typical program are externally adjusted via an external adjusting programmer so as to adapt the typical program to the needs of the patient.

The advantage of the invention is that the patient can himself adjust the operating program of his stimulator in accordance with a number of typical programs corresponding to uniform categories of effort.

BRIEF DESCRIPTION OF THE DRAWING

The other features of the invention will be clear from the following description with reference to the single accompanying drawing which illustrates the invention. The FIGURE shows the implanted programmable stimulator in conjunction with external control and adjustment programmers.

DETAILED DESCRIPTION OF THE PREFERRED EMBODIMENT

The invention relates firstly to a method of adjusting an implantable heart stimulator 1 in dependence with the effort exerted by the patient wearing the stimulator 1, using an external control programmer 2 associated in operation with the stimulator 1. The invention also relates to the implantable heart stimulator 1, the parameters of which are adjustable in accordance with the effort exerted by the patient. Finally the invention relates to the external programmer 2 for actuating the heart stimulator 1, the programmer being used for adjusting the operating parameters of stimulator 1.

In the method according to the invention, a number of typical operating programs $P_i \ldots P_i \ldots P_n$ of stimulator 1 are first defined. Each typical program $P_i$ corresponds to one kind of effort by the patient. For example, a first typical program corresponds to walking pace, a second program to climbing stairs, and a third program to a particular sport. Each typical program is characterised by specific values v of at least one operating parameter p of stimulator 1.

The various typical programs $P_i$ and consequently the corresponding specific values v of parameters p are stored in the memory of a microprocessor 3 of stimulator 1.

Next, microprocessor 3 is externally actuated, via the control programmer 2, so as to select the desired typical operating program $P_i$, whereupon the stimulator 1 operates in accordance with the selected typical programe $P_i$.

As a result, the patient wearing the stimulator 1 can independently choose a typical operating program $P_i$ for the stimulator in dependence on the effort to be accomplished, which is reduced to a typical effort corresponding to the typical program.

According to another important feature of the invention, the maximum stimulation frequency F (i.e. the parameter p) and the time D necessary for reaching this frequency are defined for each typical operating program $P_i$ of stimulator 1. Of course, the invention also applies to the case where other parameters (different and/or additional) are adjusted.

Preferably also, in the case of each typical program $P_i$, the time for which the stimulator operates at the maximum frequency F is limited to a specific preset duration T. To this end, the specific durations T of the typical programs $P_i$ are stored in the memory of microprocessor 3 (or alternatively in programmer 2).

These two features avoid abrupt, dangerous changes in stimulator frequency or excessive maintenance at the previously-mentioned frequency.

In the case for example of each program $P_i$, three specific values FI, DI and TI are defined and correspond respectively to a maximum stimulation frequency, a time necessary for reaching the maximum frequency, and a duration of operation of the stimulator at the maximum frequency. Also, a number of programs $P_1 \ldots P_i \ldots P_n$ are stored in the memory of microprocessor 3. For simplicity of operation and to prevent the memory becoming too large, the number n of stored programs is limited to a few, e.g. to a number between 3 and 10 programs. However, the invention also applies to a much larger number of stored programs.

The characteristic of each typical program $P_i$ is left to the choice of the patient and the doctor when necessary. The invention also has the advantage of great flexibility of adjustment depending on each particular case, inter alia the physiological characteristics of the patient, his activity, etc. The values given to the parameters F, D, T of each typical program P can also be chosen by the doctor.

According to another feature of the invention, a warning device 4 emits a visual and/or sound signal when the specific duration of operation of the stimulator 1 in accordance with a selected typical program $P_i$ has been reached. The signal informs the patient that the typical program has ended, particularly in the case when, as previously stated, the duration of operation of the stimulator at the maximum frequency is preset and therefore limited.

Instead of the parameter being the duration of operation of the stimulator at the maximum frequency of a typical program, the parameter can be the total duration of the typical program itself.

The fixing of a maximum duration of operation of the stimulator at the maximum frequency, combined with the presence of an end-of-program warning signal, is a security measure for informing the patient that the typical program has ended, for limiting the time during which the stimulator operates at a high frequency, and finally for forcing the patient to restart the typical program if his effort is prolonged.

Preferably, one or more transitory programs are defined for returning the operation of the stimulator and are automatically carried out at the end of each typical program $P_i$. More generally, a routine is defined for returning the stimulator 1 to the normal operating conditions. For safety reasons, the return is brought about gradually.

In another preferred embodiment of the invention, the specific values v of the parameters P of each typical program V are externally adjusted, by an external adjusting programmer 5, so as to adapt the typical program $P_i$ to the patient's needs. In that case the method is organized so that each program and each parameter of each program is called in succession.

A heart stimulator 1 according to the invention is of a known multiprogrammable kind and comprises an outer casing 6 and an output 7 for connecting an electrode 8 (shown in part). Casing 6 contains an electric battery, e.g. a lithium battery, an electronic control circuit associated with the battery and with output 7, and a microprocessor 3 for working the method.

The casing 6, the electric output 7, the electrode 8, the battery and the electronic circuit of stimulator 1 are not in themselves directly part of the invention and are generally well known to the skilled addressee in the case of a multiprogrammable stimulator. For this reason these various constituents are not described in greater detail here.

A number of typical operating programs $P_i$ characterised by specific values v of at least one operating parameter p of the stimulator are stored in the memory of microprocessor 3. Stimulator 1 also comprises means for selecting a typical operating program $P_i$, i.e. specific values corresponding to the parameters p, the selection being made by external means, i.e. across the cutaneous barrier 9 of the patient.

As previously stated, the operating parameters p, the specific values v for which are stored in the memory of microprocessor 3, are the maximum stimulation frequency F and/or the time D for reaching the frequency F and/or the duration of operation T of the stimulator at the maximum frequency.

Also, a transitory program for returning the operation of stimulator 1 to normal conditions is also stored in the memory of microprocessor 3 and is automatically used at the end of each typical program $P_i$.

The selection means comprise control-instruction receiving means associated with the microprocessor 3 and adapted to be coupled to the external control programmer 2. Preferably, the same or other adjusting-instruction receiving means are also associated with microprocessor 3 and adapted to be coupled to an external adjusting programmer 5.

Note that external adjustment of a parameter of a multiprogrammable heart stimulator is known per se and the invention therefore uses these known means. for example the receiving means can be an antenna receiving radio-electric signals or a REED switch receiving pulsed magnetic fields of the stimulation electrode 8 receiving galvanic currents.

A possible structural embodiment of an aforementioned programmable heart stimulator is described e.g. in French PS 2 424 737. For example, the RAM of microprocessor 3 is structured in registers corresponding to a combination of groups corresponding to the number of typical programs and adjustable parameters in the typical programs.

In practice, the values v of parameters p can vary within relatively wide limits. For example the frequency can vary between 40 and 160 beats per minute and the time D and T can vary between a few minutes and about 1 hour.

The external control programmer 2 comprises at least one selector 10 of a typical program from among a number of typical programs characterised by specific values v of at least one operating parameter p of stimulator 1 as previously stated.

In one possible embodiment, the control programmer 2 comprises a casing 11, a source of electric energy 12 such as a battery disposed in casing 11, electric contacts 13 emerging from casing 11 and used for transmitting electric pulses to the heart stimulator so as to actuate it, and an electronic circuit 14 also disposed in casing 11 and associated with the electric energy source 12, contacts 13, and selector 10. Electronic circuit 14 is adapted to supply contacts 13 with specific pulses trains depending on the state of selector 10. Selector 10 can e.g. comprise a set of keys, i.e. a "stop-go" key 15 and keys 16 each corresponding to a typical program.

An aforementioned programmer 2 can operate as follows: When programmer 2 is started by actuating the key 15, a first pulse train is emitted by circuit 14 and transmitted to stimulator 1 via contacts 13 and the receiving means on the stimulator. The first pulse train is e.g. such that its length is greater than any programmable refractory period of stimulator 1. As soon as it detects an aforementioned pulse train, the heart stimulator 1 automatically adjusts to the operating mode called VVT in which a signal is emitted in synchronism with any detected signal. Next, the pulse train is emitted or not emitted after each pulse, and the resulting presence or absence of a pulse train corresponds to a binary item 0 or 1 transmitted to microprocessor 3 and used for adjusting it. For safety reasons, redundance is established among the signals emitted by programmer 2.

Programmer 2 can also comprise a warning device 4 associated in operation with the electronic circuit 14 and with a logic unit for operating the programmer 2, with a view to emitting a visual or sound signal at the end of every typical program or, if required, as a warning before the end of the program.

Of course, there can be numerous variants of programmer 2, more particularly relating to the means of communicating with the stimulator 1 used.

Finally the invention can also make use of a known adjusting programmer 6, which is applied for an original purpose for adjusting the values of various parameters p in conjunction with the typical programs $P_2$.

With regard to stopping the selected typical program, there are two possible cases: either the stoppage is voluntary and made by the patient himself, using the stop go-key 15, or the stoppage is automatic on reaching the maximum pre-programmed duration of operation T. In the latter case, two variant embodiments are possible. Either the duration T is stored in the memory of the microprocessor (3) or it is stored in the logic unit for operating the programmer 2.

I claim:

1. A method of externally adjusting an implanted heart stimulator in accordance with the effort exerted by a patient wearing the stimulator that is normally operating at a starting condition, said adjustment being accomplished by an external control programmer, said method comprising the steps of:

defining in said stimulator a plurality of operating programs, each program corresponding to a type of effort by the patient;

storing in the stimulator, for each of the operating programs, a maximum stimulation frequency and a present time within to the frequency;

selecting a desired operating program within said stimulator by activating said external control programmer, the selecting of the desired program being made in dependence on the effort exerted by the patient;

operating the stimulator is accordance with the selected operating program; and automatically returning the operation of the stimulator to said starting condition at the end of the operation of the selected operation program.

2. The method according to claim 1, wherein for each operating program, the duration of operation of the stimulator at the maximum frequency is limited to a preset specific duration stored in said stimulator.

3. The method according to claim 2, further comprising the step of emitting a visual and/or sound warning signal on reaching the specific duration of operation of the stimulator in accordance with the selected operating program.

4. An implantable heart stimulator normally operating at a starting condition and externally adjustable in accordance with effort exerted by a patient wearing the stimulator, said adjustment being accomplished by an external control programmer, said stimulator comprising:

memory means for storing a plurality of operating programs, each program corresponding to a type of effort exerted by the patient, and having associated with it a maximum stimulation frequency and a preset time within which to reach said maximum stimulation frequency;

means for selecting a desired operating program within said stimulator in response to an activation signal provided by said external control programmer, the selection of said desired program being made in dependence on the effort exerted by the patient;

means for operating the stimulator in accordance with the selected operating program; and means for automatically returning the operation of the stimulator to the starting condition at the end of the operation of the selected operating program.

5. The stimulator according to claim 4, wherein for each operating program, the duration of operation of the stimulator at the maximum frequency is limited to a preset specific duration.

* * * * *